United States Patent [19]
Shipp

[11] Patent Number: 6,031,526
[45] Date of Patent: Feb. 29, 2000

[54] VOICE CONTROLLED MEDICAL TEXT AND IMAGE REPORTING SYSTEM

[75] Inventor: John I. Shipp, Tullahoma, Tenn.

[73] Assignee: Apollo Camera, LLC, Tullahoma, Tenn.

[21] Appl. No.: 08/695,081

[22] Filed: Aug. 8, 1996

[51] Int. Cl.[7] .................................................... G06F 17/21
[52] U.S. Cl. ........................................ 345/302; 707/530
[58] Field of Search ............................... 345/302; 705/3; 707/500, 515, 526, 530

[56] References Cited

U.S. PATENT DOCUMENTS

| | | | |
|---|---|---|---|
| 4,344,682 | 8/1982 | Hattori | 354/62 |
| 4,651,202 | 3/1987 | Arakawa | 358/98 |
| 5,241,472 | 8/1993 | Gur et al. | 382/128 |
| 5,309,895 | 5/1994 | Yabe | 128/6 |
| 5,311,859 | 5/1994 | Monroe et al. | 126/6 |
| 5,363,839 | 11/1994 | Lankford | 128/9 |
| 5,365,267 | 11/1994 | Edwards | 348/65 |
| 5,553,609 | 9/1996 | Chen et al. | 600/301 |
| 5,838,313 | 11/1998 | Hou et al. | 345/302 |

FOREIGN PATENT DOCUMENTS 0025967  9/1980  European Pat. Off. .......... A61B 1/00

OTHER PUBLICATIONS

"Consumer Electronics: Consumer Electronics Notebook." (Aug. 21, 1995): 13.

Benham, D. & Fischer, M.L. "Communications News: Video Network Boosts Fairchild Productivity." (Feb. 1, 1983): vol. 20, No. 2, p. 2.

Laplante, Alice. "InfoWorld: Enterprise Computing/Management; Case Study." (Mar. 22, 1993): 64.

Med Images, Inc. "Integrated Documentation Services".

*Primary Examiner*—James P. Trammell
*Assistant Examiner*—John Leonard Young
*Attorney, Agent, or Firm*—Waddey & Patterson; Mark J. Patterson

[57] ABSTRACT

A system for generating electronic and printed medical records provides automatic integration of captured video still images and voice dictated information concerning the image. A voice recognition module allows the system to respond to voice commands and automatically transcribes the dictated text into a word processing document.

14 Claims, 2 Drawing Sheets

OPERATIVE NOTE

DIAGNOSIS: CHOLELITHIASIS, CHRONIC CHOLECYSTITIS WITH RECENT GALLSTONE PANCREATITIS.

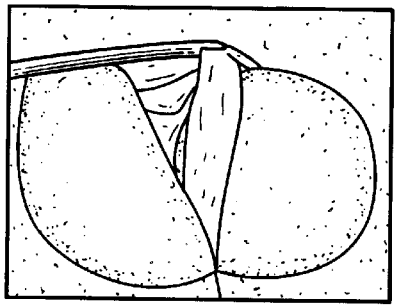 

PHOTO 1.
GALLBLADDER AS INITIALLY VISUALIZED

PHOTO 2.
CYSTIC ARTERY DEMONSTRATED

OPERATION PERFORMED: LAPAROSCOPIC CHOLECYSTECTOMY WITH INTRAOPERATIVE CHOLANGIOGRAM.

PROCEDURE: WITH THE PATIENT IN THE SUPINE POSITION ON THE OPERATING TABLE AND UNDER GENERAL ENDOTRACHEAL ANESTHESIA, THE ABDOMEN WAS PREPPED WITH BETADINE AND DRAPED INTO A STERILE FIELD. WITH THE PATIENT THEN IN TRENDELENBURG POSITION, $CO_2$ INSUFFLATION OF THE PERITONEAL CAVITY WAS ACHIEVED WITH THE VERRES NEEDLE THROUGH A 1 CM UMBILICAL INCISION. A 10 MM TROCAR WAS THEN INSERTED AND EXPLORATION WITH THE LAPAROSCOPE CARRIED OUT. THE PATIENT WAS THEN PLACED IN REVERSE TRENDELENBURG, TILTED TO THE LEFT, AND THREE ADDITIONAL EPIGASTRIC TROCARS WERE PLACED UNDER DIRECT VISION. A 10 MM ONE WAS PLACED 5 CM BELOW THE XIPHOID TO THE RIGHT OF THE MIDLINE, AND TWO 5 MM ONES WERE PLACED TWO FINGERBREADTHS AND THREE FINGERBREADTHS BELOW THE COSTAL MARGIN IN THE MIDCLAVICULAR AND ANTERIOR AXILLARY LINE RESPECTIVELY. THE GALLBLADDER WAS THEN GRASPED AND RETRACTED CEPHALAD.

THE GALLBLADDER WAS ENFOLDED IN THE LOBES OF THE RIGHT LOBE OF LIVER, AS SHOWN IN PHOTO 1.

*FIG. 2*

VOICE CONTROLLED MEDICAL TEXT AND IMAGE REPORTING SYSTEM

BACKGROUND OF THE INVENTION

The present invention relates generally to the generation of reports of medical treatments and procedures and more particularly to a voice recognition system for electronically capturing images from a video camera and combining them with dictated text into an integrated medical report and patient record.

Most physicians generate notes describing their observations either while performing or immediately after performing surgery or other medical procedures. Usually, these notes are dictated by the physician and later manually transcribed by a stenographer into a written report. These reports are then used for patient education, referral reports, marketing efforts, archiving, and to comply with regulatory requirements.

Due to an increased use of video cameras in surgical procedures, images are now frequently available to supplement the dictated notes. However, most hospitals do not have the equipment required to print high quality still color images from a video imaging system so that they can be incorporated, along with the transcribed observations of the physician, in the patient's permanent medical record.

Software is available in the art that allows images derived from a video camera system to be printed directly into a document or report which also contains the surgeon's notes. Such systems, available for example from Med Images, Inc. of Knoxville, Tenn., "grabs" a video frame on command of the surgeon and stores the "grabbed" image frames so that the surgeon can later view them as he or she dictates a description of the procedure and other comments regarding the images. The images and dictated audio information are then transmitted to a central transcription location by a modem. The audio information is then transcribed by a stenographer and printed onto a report onto which the grabbed still images have been printed.

The problem with these prior art systems is that the reports are expensive to produce because the color images and audio data must be must transmitted via modem to the central location where the report is then prepared in a two step process. That is, the audio information must be transcribed and formatted in a word processor by the stenographer. Because the stenographer and surgeon are working in separate locations, editing of the report presents a significant problem. For example, questions concerning certain unclear passages must be answered through telephone conversations but the surgeon often is not immediately available. In addition, dictated passages that are transcribed incorrectly must be corrected by the stenographer after a call or letter from the surgeon. This requires reprinting and re-delivery of the finished report.

In the prior art medical record reporting systems, the transcribed information is printed, using a standard laser printer, with spaces or regions left blank on the page for the color images which are then added during a second printing step, using an expensive high resolution drum printer. This is a cumbersome process due to problems in registering the printing of the images within the blank regions adjacent the pre-existing printed text. After the completed report is proofread, it is delivered to the hospital or surgeon's office, usually using an expensive overnight delivery service.

What is needed, then, is a system whereby still electronic images captured from a video camera during surgery can be stored electronically at the command of the surgeon and automatically combined with readable text generated from the surgeon's oral comments.

SUMMARY OF THE INVENTION

An object of the present invention is to allow a physician to capture a selected still image from a video camera being used during a medical procedure and associate the image with the physician's dictated observations.

Another object of the present invention is to provide a system in which the physician's dictated observations are electronically transcribed and converted into electronic readable and editable text in a word processing document which includes a viewable image.

Yet another object of the present invention is to provide a system for generating medical records which responds to voice commands of the user.

In accordance with these and other objects of the present invention which will be apparent to those skilled in the art, the system of the present invention provides an interface to a conventional video camera used during surgical procedures. In addition to allowing for real-time viewing of the video images on a video monitor, a video processor of the system continuously provides individual video frames to a frame storage unit. In response to a verbal or manual command by the physician, the frame storage unit captures a selected video frame for eventual integration into a printed medical record.

In addition, the physician dictates his or her observations concerning the medical procedure and captured video frame. A voice recognition module converts the dictated audio information into viewable and editable text which is combined in a word processing module with the captured video frame. The captured video frame is integrated with the dictated text and then constitutes an electronic medical record which can be edited and viewed as well as printed on a conventional color laser printer.

BRIEF DESCRIPTION OF THE DRAWINGS

FIG. 2 represents a typical medical record generated by the system of the present invention in which a video image has been captured and electronically integrated with text transcribed using voice recognition.

DESCRIPTION OF THE PREFERRED EMBODIMENT

Figure 1:
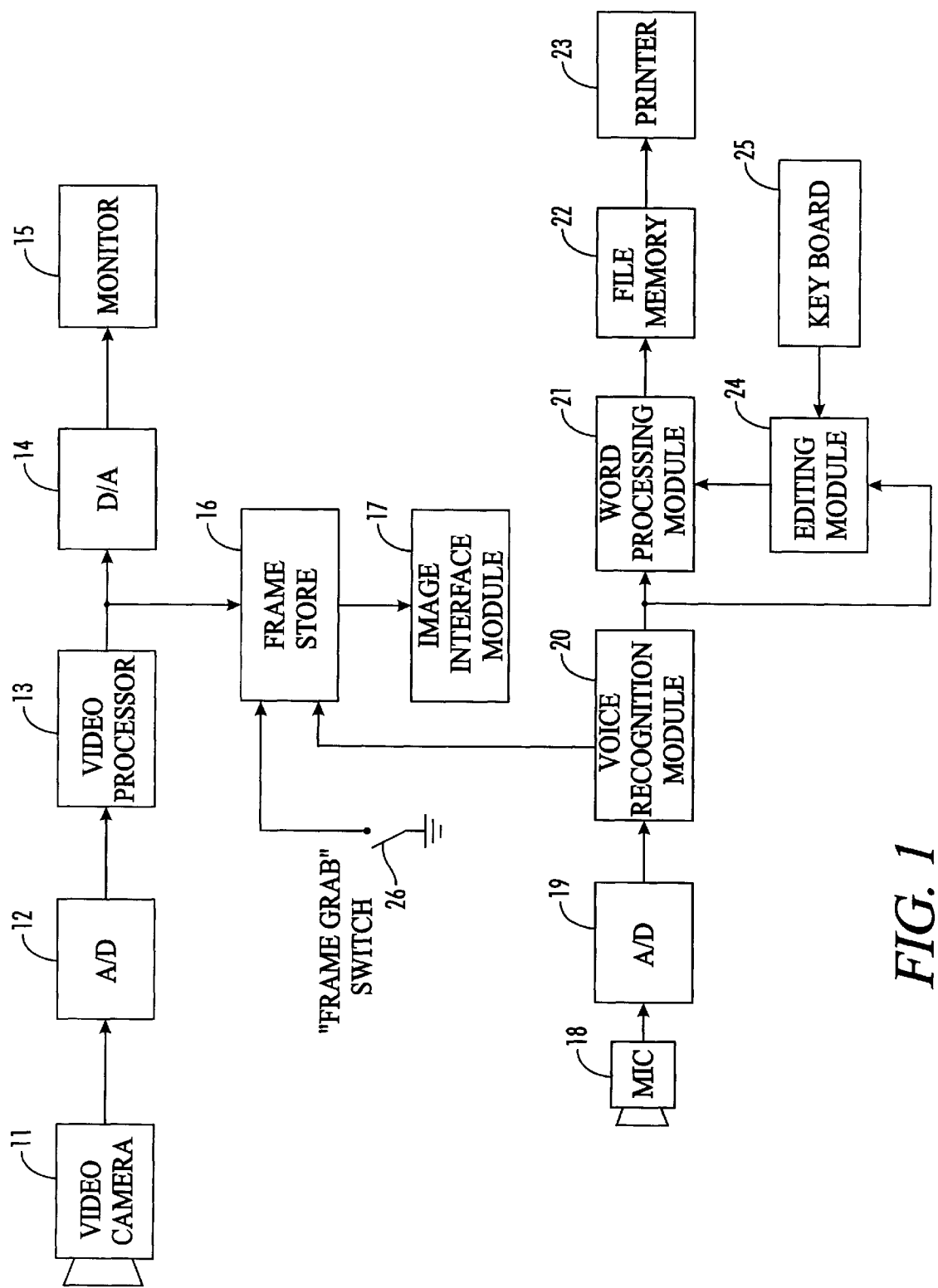
FIG. 1 is a block diagram of the system of the present invention.

A block diagram of system 10 of the present invention is shown in FIG. 1. A conventional video camera 11 such as a CCD camera used with an endoscope or other surgical imaging device, provides a conventional analog video output to analog to digital (A/D) converter 12, where the video signals from camera 11 are digitized and passed through to video processing unit 13. Video processing unit prepares the video data for subsequent viewing and/or storing. An example of a preferred method of capturing and processing the video data is described in U.S. Pat. No. 5,264,925 for a "Single Sensor Video Imaging System and Method Using Sequential Color Object Illumination." The digitized and processed video data is then sent to a conventional digital to analog (D/A) converter 14 where it is converted back to an analog video format for immediate, real-time display on a conventional video monitor 15.

In addition, the continuous digital output from video processing unit 13 is transmitted to a video frame storage unit 16, which has an electronic memory capable of storing discrete digitized video images captured by video camera 11 and processed through A/D converter 12 and video processor 13. Although the output of video processor 13 is continuously provided to frame storage device 16, in the preferred embodiment the storage of a specific still video image is activated only when the surgeon or other user of the system selects a specific image and activates frame storage unit 16, such as by manually closing frame grab switch 20. A Hitachi HM530281 can be used as the frame storage unit 16.

During or after the surgical procedure, the surgeon speaks into a conventional microphone 18, dictating pertinent information describing the medical procedure and specifically relating those observations to the images viewed by the surgeon on monitor 15 which are selected for capturing and storing in frame storage unit 16. The analog audio data is digitized in A/D converter 19 in conventional fashion and transmitted to a voice recognition module 20. Typically, voice recognition module 20 will include proprietary software and hardware, in the form of an add-in card for a conventional personal computer (PC), whereby the proprietary software recognizes patterns corresponding to specific words or phrases within the digitized data stream coming from A/D converter 19. Hardware and software which can be used for voice recognition module 20 is available from Phillips. A National ADC0804 device can be used as A/D converter 19.

The output of voice recognition module 20 preferably constitutes electronic text containing digitized character and formatting codes recognized by standard word processing software, such as Microsoft Word. Accordingly, word processing module 21 includes both hardware and software which receives the output from voice recognition module 20 and converts it into an editable and readable electronic document for ultimate display on a personal computer monitor (not shown) and for storage in volatile or non-volatile computer memory 22.

Following dictation of the surgeon's observations, and voice and word processing of the resulting audio data, the electronic document can be edited using editing module 24 (also available from Phillips in conjunction with their speech recognition software, either by voice commands received from voice recognition module 20 or from keyboards commands entered at a standard personal computer keyboard 35.

Voice recognition module 20 also includes software implemented algorithms which have been taught to recognize certain words or word combinations as voice commands, including system operation and/or text editing commands. Accordingly, when the predetermined voice command is given by the user through microphone 18, an electronic link between voice recognition module 20 and frame storage device 16 allows for a frame grab command to be delivered to frame storage device 16. In addition, when the system 10 is in the editing mode, editing commands spoken by the user are recognized and interpreted by voice recognition module. Corresponding editing codes are then sent to editing module 24 which causes word processing module 21 to edit the text accordingly.

Video still frames which are stored temporarily in frame storage unit 16 pass to word processing module 21 through an image interface module 17. Image interface module 17 reassembles and formats the digitized video frames stored in frame storage unit 16 into electronic images having standardized graphics protocol (e.g., JPEG, GIF) which is readable by the software associated with the word processing module 21. Accordingly, the electronic images representing the stored frames are converted by word processing module 21 into viewable images and directly integrated into an electronic word processing document or medical report, along with the electronic document containing the text dictated by the surgeon. The combination of the readable text and a viewable image then constitutes a comprehensive medical record which can be stored in memory 22, for ultimate printing in a report by a laser or other color text and graphics printer 23.

Thus, although there have been described particular embodiments of the present invention of a new and useful Voice Controlled System for Generating Medical Records Combining Text and Images, it is not intended that such references be construed as limitations upon the scope of this invention except as set forth in the following claims.

What I claim is:

1. A system for generating a medical record comprising:
   a. video camera interface means to receive and process video data from a video camera, the video data including a series of video frames;
   b. video frame storage means operatively connected to the video camera interface means to electronically store at least one of the video frames;
   c. image interface means for converting the stored video frames into electronic images, the image interface means operatively connected to the video frame storage means;
   d. audio interface means to receive and process audio data, the audio data including medical information associated with a particular electronic image which is dictated by a user of the system;
   e. voice processing means, operatively connected to the audio interface means, for processing the audio data, the processing of the audio data including converting the dictated medical information into electronic text; and
   f. word processing module means for converting the electronic text into readable text, for converting the electronic images into viewable images, and for integrating the viewable images into the medical record with corresponding portions of the readable text, to create a printable and viewable electronic medical record combining the viewable images with the readable text dictated by the user.

2. The system of claim 1 further comprising frame selection means for causing the frame storage means to store a video frame in response to a selection made by the user of the system.

3. The system of claim 2 wherein the audio data includes voice commands dictated by the user of the system, the processing of the audio data includes processing the voice commands to recognize a frame grab command, and the frame selection means comprising voice activated switch means to activate the frame storage means in response to the frame grab command, the voice activated switch means electronically linking the voice processing means and the frame storage means.

4. The system of claim 3, the voice processing means including A/D converter means to digitize the audio data.

5. The system of claim 4 further comprising editing means to edit the readable text.

6. The system of claim 5 where the voice commands include editing commands, the processing of the audio data includes processing the voice commands to recognize the editing commands, and the editing means includes means associated with the word processing module means for responding to the editing commands.

7. A system for making a record of a medical procedure comprising:
   a. a video camera;
   b. means to convert analog video data from the video camera to digitized video data;
   c. means to electronically store the digitized video data in individual frames corresponding to a selected still image of the medical procedure;
   d. means to electronically convert spoken words and phrases into digitized audio data; and
   e. means to electronically combine the individual frames of digitized video data with the digitized audio data into a word processing document which integrates for viewing and printing viewable and editable text representing the spoken words and phrases and viewable images representing the selected still images.

8. The system of claim 7 further comprising means to select the still images of the medical procedure to be stored by the system in response to voice commands.

9. The system of claim 7 further comprising means to edit the word processing document.

10. The system of claim 9 further comprising means to view the analog video data as it is being received from the video camera.

11. The system of claim 10 further comprising means to print the word processing document.

12. A method of generating a record of a medical procedure, the record containing both an image and text associated by a physician with the image, the method comprising the steps of:
   a. capturing the image with a video camera and electronically storing the image;
   b. capturing voice dictation of the physician associated with the image;
   c. converting the captured voice dictation in a voice recognition and processing module into electronic text readable by a word processing module;
   d. converting the image which has been electronically stored into a converted image having a graphics format readable by the word processing module; and
   e. electronically combining the converted image with the electronic text in the word processing module to create a printable and viewable electronic medical record of the procedure.

13. The method of claim 12 further comprising the step of printing the electronic medical record.

14. The method of claim 12 further comprising the step of automatically capturing the image in response to a voice command from the physician.

* * * * *